United States Patent
McKinnon et al.

(10) Patent No.: US 8,361,038 B2
(45) Date of Patent: Jan. 29, 2013

(54) SYSTEMS AND METHODS FOR PROVIDING A FLOW CONTROL VALVE FOR A MEDICAL DEVICE

(75) Inventors: Austin Jason McKinnon, Herriman, UT (US); S. Ray Isaacson, Roy, UT (US); Marty L. Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 340 days.

(21) Appl. No.: 12/703,406

(22) Filed: Feb. 10, 2010

(65) Prior Publication Data
US 2010/0204660 A1   Aug. 12, 2010

Related U.S. Application Data

(60) Provisional application No. 61/151,773, filed on Feb. 11, 2009.

(51) Int. Cl.
*A61M 5/00* (2006.01)
(52) U.S. Cl. .................. 604/244; 604/246; 604/249
(58) Field of Classification Search ............ 604/164.01, 604/164.02, 167.01–167.06, 168.01, 172, 604/200, 244, 246, 249
See application file for complete search history.

(56) References Cited

U.S. PATENT DOCUMENTS

| | | |
|---|---|---|
| 4,387,879 A | 6/1983 | Tauschinski |
| 4,449,693 A | 5/1984 | Gereg |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |

(Continued)

FOREIGN PATENT DOCUMENTS

| | | |
|---|---|---|
| CA | 2133053 A1 | 3/1995 |
| DE | 20 2009 009 602 U1 | 1/2010 |
| EP | 1 679 043 A1 | 7/2006 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Theodore Stigell
(74) *Attorney, Agent, or Firm* — Jeanne Lukasavage; Craig Metcalf; Kirton McConkie (57) ABSTRACT

The present invention relates generally to a vascular access device having a septum positioned within a lumen of the device, the device further having a pusher for providing a fluid pathway through the septum. In particular, the present invention relates to systems and methods for improving flow of a fluid through the access device, while minimizing stagnation of fluids within the device. These systems and methods include various modified fluid pathways and interactions between the vascular access device body, the septum and the pusher.

6 Claims, 12 Drawing Sheets

U.S. PATENT DOCUMENTS

| | | |
|---|---|---|
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A * | 10/1999 | Pike .................. 251/149.1 |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2010/0204675 A1 | 8/2010 | Woehr et al. |
| 2010/0222746 A1 | 9/2010 | Burkholz |

FOREIGN PATENT DOCUMENTS

| | | |
|---|---|---|
| WO | WO 99/34849 | 7/1999 |
| WO | 2008/052790 A2 | 5/2008 |
| WO | 2009/114833 A1 | 9/2009 |
| WO | 2010/093791 A1 | 8/2010 |

* cited by examiner

SYSTEMS AND METHODS FOR PROVIDING A FLOW CONTROL VALVE FOR A MEDICAL DEVICE

RELATED APPLICATIONS

This application claims the benefit of U.S. Provisional Patent Application Ser. No. 61/151,773 entitled CATHETER VALVE ASSEMBLY, filed on Feb. 11, 2009 and incorporated herein in its entirety.

BACKGROUND OF THE INVENTION

The present disclosure relates to fluid flow in extravascular systems used to provide infusion or other therapy to patients. Infusion therapy is one of the most common health care procedures. Hospitalized and home care patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by vascular access devices located outside the vascular system of a patient. An extravascular system includes at least one vascular access device and/or other medical device that may access a patient's peripheral or central vasculature, either directly or indirectly. Vascular access devices include closed access devices, such as the BD Q-SYTETM closed Luer access device of Becton, Dickinson and Company; syringes; split access devices; catheters; and intravenous (IV) fluid chambers. An extravascular system may access a patient's vascular system for a short term (days), a moderate term (weeks), or a long term (months to years), and may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

Although several techniques for placing such catheters are practiced in the art, many generally include the step of inserting at least a portion of the needle into the target vessel and then sliding the catheter over the needle into place. The medical worker attempts to verify proper placement of the catheter within the blood vessel. Catheter and introducer needle assemblies have been provided that include means for verifying proper placement of the catheter in a blood vessel such as a flashback chamber in the catheter hub or a notch in the introducer needle.

Once placement of the needle has been confirmed by the observation of flash, the user may temporarily occlude flow in the blood vessel at the catheter tip, remove the needle, leaving the catheter in place, and attach a device to the catheter for fluid removal, input, or to seal the catheter. This process has been somewhat difficult in practice since many placement sites simply do not allow easy occlusion of the target vessel. Additionally, even when such occlusion is achieved, it may be imperfect, thus resulting in blood leaking from the catheter, endangering the medical personnel employing it.

Catheter and introducer needle assemblies have thus been provided in the art that provide a variety of seals or valve mechanisms for preventing outflow of fluid during and following removal of the introducer needle. These structures are generally elastomeric plates designed to closely conform to the shape of a needle during storage and use to prevent leaking, then to seal upon removal of the needle. In an ideal vascular access device, the septum would continuously seal the patient's vascular system, which may include external vascular equipment intentionally coupled to the patient's internal vascular system by a medical practitioner, from the external environment.

Complications associated with infusion therapy include significant morbidity and even mortality. Such complications may be caused by regions of stagnant fluid flow within the vascular access device or nearby areas of the extravascular system. These are regions in which the flow of fluid is limited or non-existent due to the conformation of the septum or valve mechanism in the extravascular system or the fluid dynamics within that area of the extravascular system. Blood, air bubbles or infused medications may become trapped within these regions of stagnant flow as a result of the limited or non-existent fluid flow. When blood is trapped within the extravascular system bacteria can breed which can lead to infections. When a different medication is infused into the extravascular system, or the extravascular system is exposed to physical trauma, the extravascular system's fluid flow may become altered, releasing trapped air bubbles or residual medications back into the active fluid path of the extravascular system. This release of air bubbles and residual medication into the active fluid path extravascular system may result in significant complications.

Released air bubbles may block fluid flow through the extravascular system and prevent its proper functioning. More seriously, released air bubbles may enter the vascular system of the patient and block blood flow, causing tissue damage and even stroke. In addition, residual medications may interact with presently infused medications to cause precipitates within the extravascular system and prevent its proper functioning. Furthermore, residual medications may enter the vascular system of the patient and cause unintended and/or undesired effects.

Therefore the need exists for valve mechanisms in vascular access devices that eliminate, prevent, or limit regions of stagnant flow vascular access devices and extravascular systems to provide better flush properties.

SUMMARY OF THE INVENTION

The various embodiments of the present invention provide a number of flow control valve mechanisms which eliminate or reduce areas of low or no fluid flow occurring within a vascular access device.

According to one aspect, a vascular access device comprises a body including a first lumen extending therethrough and a flow control valve, including a septum, and a pusher having a distal end, a proximal end, an outer surface, a second lumen therethrough, and at least one flow channel.

According to another aspect, a vascular access device comprises a body including a first lumen extending therethrough and a flow control valve, including a septum, a pusher having a distal end, a proximal end, an outer surface, a second lumen therethrough, and at least one rib.

These and other features and advantages of the present disclosure may be incorporated into vascular access devices and will become more fully apparent from the following description and appended claims, or may be learned by the practice and implementation of the present disclosure. As described above, the present disclosure does not require that all of the features described herein be incorporated into every embodiment nor is it required that certain features be used exclusive of other features. Vascular access devices within the scope of the present disclosure may include one or more combinations of the features described herein.

DETAILED DESCRIPTION OF THE INVENTION

It will be readily understood that the components of the present disclosure, as generally described and illustrated in the figures herein, could be arranged and designed in a wide variety of different configurations. Although the embodiments of this invention are described herein in connection with an IV catheter, it is to be understood that this invention is applicable to other catheters. For example, this invention is applicable to standard peripheral IV catheters, extended dwelling catheters requiring the needle to be connected to the needle hub by a stylet as well as other medical devices where it is desirable to include a septum to regulate the flow of fluid into or out of a space. Thus, the following more detailed description, as represented in the figures, is not intended to limit the scope of the disclosure, but is merely a representative of exemplary combinations of the components.

The term "proximal" is used to denote a portion of a device which, during normal use, is nearest the user and furthest from the patient. The term "distal" is used to denote a portion of a device which, during normal use, is farthest from the user wielding the device and closest to the patient. The term "activation" of a valve mechanism is used to denote the action of opening or closing of such a valve.

Figure 1:
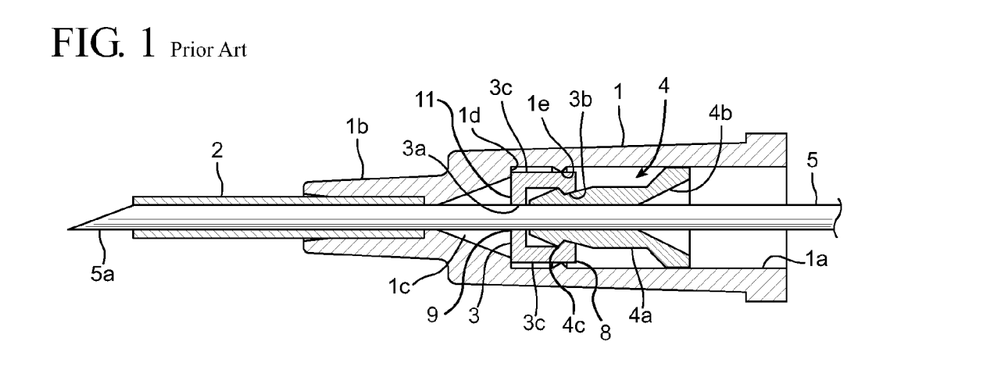
FIG. 1 is a cross section view of an indwelling catheter having a prior art flow control valve mechanism.

An example of a prior art extravascular system is disclosed in U.S. Pat. No. 7,008,404 and shown in FIGS. 1 to 3. An indwelling catheter has, as shown in FIG. 1, a hollow catheter body 1, a catheter 2 fitted into a holder 1b provided at a distal end of the catheter body 1, a septum 3 fitted inside the catheter body 1, and a hollow pusher 4 slidably fitted inside the catheter body 1. The catheter tube 2, septum 3, and the pusher 4 are coaxially aligned in this order.

The catheter body 1 has a tubular shape. The inner surface 1a of the catheter body lumen is tapered toward the distal end, with a gradually reduced diameter. The catheter body 1 is preferably of a transparent or semi-transparent material so as to show the interior, enabling checking of movement inside. Suitable materials for catheter body 1 include, but are not limited to, thermoplastic polymeric resins such as polycarbonate, polystyrene, polypropylene and the like.

The catheter 2 is press-fitted into the tube holder 1b which communicates at its proximal end with the inside of the catheter body 1. It is preferred that a lubricating coating is provided to the entirety or part of the catheter 2 so as to reduce resistance caused by insertion through skin or into a blood vessel. Suitable materials for catheter 2 include, but are not limited to, thermoplastic resins such as fluorinated ethylene propylene (FEP), polytetrafluoroethylene (PTFE), polyurethane and the like. Preferably, catheter 2 is formed from a thermoplastic hydrophilic polyurethane that softens with exposure to physiological conditions present in the patient's body.

The septum 3 is of a generally tubular shape having a proximal end 8 and a membrane section 9 having a planar flat surface located at the distal end 11. Typically, septum 3 further includes a single needle slit 3a or valve aperture located about the centre of membrane section 9, extending through membrane section 9, to facilitate penetration of septum 3 by introducer needle 5 having a needle tip 5a. The opposing slit surfaces of the needle slit 3a are designed to closely conform to the shape of introducer needle 5 during storage and prevent an outflow of fluid during and following removal of the introducer needle 5, then to seal upon removal of the introducer needle 5. With the pusher 4 inserted therethrough, slit 3a expands forward in the distal direction and opens, providing fluid communication between the catheter 2 and the rear of the catheter body 1. An annular protrusion 3b is provided on the inner surface of a rear opening of the septum 3, to engage shoulder 4c at the distal end of the pusher 4 so as to limit the movement of pusher 4 in the proximal direction and prevent the dislocation of the pusher 4 from septum 3. A plurality of gaps 3c are defined between an outer periphery of the septum 3 and the inner surface 1a of the catheter body 1. Distal and proximal spaces divided by the septum 3 communicate with each other through the gaps 3c. Thus the septum 3 slides smoothly with air passing through the gaps 3c.

The pusher 4 is typically made from a rigid thermoplastic material or a like material, and has a lumen 7 extending therethrough. The pusher 4 has a tubular portion 4a, a conical flange 4b connected to the rear proximal end of the tubular portion 4a, and a shoulder 4c protruding from an outer periphery of the tubular portion 4a. Thus, an annular shaped interstitial space is created between tubular portion 4a and the inner surface 1a of the catheter body 1. The distal front end of the tubular portion 4a is chamfered to facilitate its penetration into slit 3a of the septum 3, and is slidably supported by the annular protrusion 3b of the septum 3. The conical flange 4b has a conical inner surface so as to facilitate insertion of the needle 5 thereinto. The peripheral surface of the flange 4b contacts the inner surface 1a of the catheter body 1 and serves to provide stability to the pusher 4 and maintain the coaxial position with respect to the catheter 2. However the peripheral surface of the flange 4b does not form a fluid seal with inner surface 1a.

The indwelling catheter is prepared for use in such a state as shown in FIG. 1 with the front end of the needle 5 protruding from the front end of the catheter 2. In this state, the needle 5 penetrates through the septum 3, providing water-tight connection therebetween, and thereby prevents blood leakage.

Figure 2:
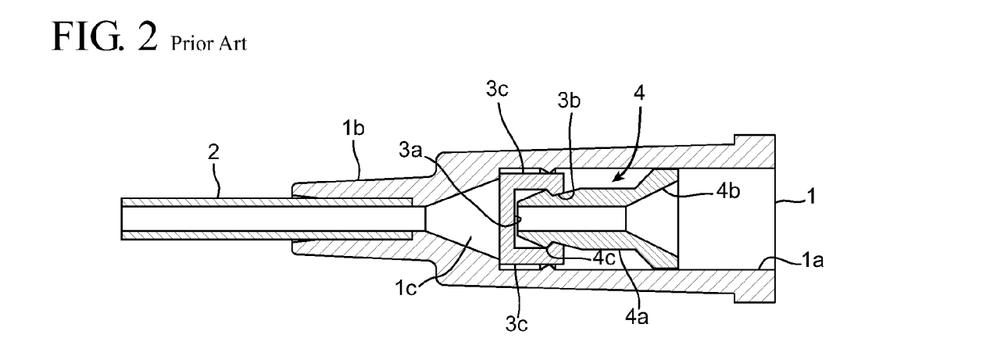
FIG. 2 is a cross section view of the indwelling catheter having a prior art flow control valve mechanism of FIG. 1 with a needle removed.

The indwelling catheter in this state is inserted into the body of a patient. Then, as shown in FIG. 2, the needle 5 is removed with the tube 2 retained in the body of the patient. Septum 3 maintains a fluid seal upon removal of needle 5, being retained by an annular protrusion 1e and a cavity edge 1d. Pusher 4 is retained in a proximal position by the interaction of annular protrusion 3b and shoulder 4c.

Figure 3:
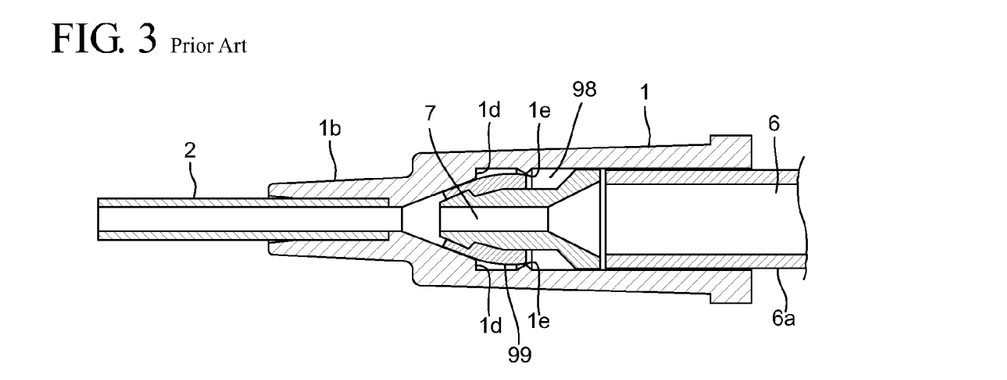
FIG. 3 is a cross section view of the indwelling catheter having a prior art flow control valve mechanism of FIG. 2 with a connector from a vascular access device connected thereto.

A connector 6 (e.g. a luer connector) of a vascular access device is then inserted from the proximal end of the catheter body 1. When pressed into the catheter body 1, the connector 6 pushes at its distal end the pusher 4. The pusher 4 thus slides forward in distal direction to press the slit 3a of the septum 3 open, thereby activating the flow control valve to the open position. Septum 3 is then pressed against the inner surface of a tapered cavity 1c of the catheter body 1 which stops the forward movement of the pusher 4 at a distal position as shown in FIG. 3, thus providing communication between the catheter 2 and the vascular access device via the lumen 7 of the pusher 4. The tapered inner surface 1a of the catheter body 1 allows for smooth insertion of the connector 6 and tight contact between an outer surface 6a of the connector 6 and the inner surface 1a through press fitting in order to prevent fluid leaking out of the proximal end of catheter body 1.

However, it should be noted that this valve mechanism has problems in regard to fluid flow and flush properties. First, fluid flow will follow the path of least resistance and in the valve mechanism shown in FIGS. 1 to 3 the majority of the fluid flow occurs through lumen 7 of pusher 4 as this is the largest opening. This results in a stable laminar fluid flow (with minimal fluid turbulence) through the valve mechanism which causes the highest degree of flow to occur at the center of lumen 7 and the center of the lumen in the catheter body 1 and the lowest degree of fluid flow to occur at the periphery of the lumen of catheter body 1. Thus areas of low or no fluid flow can occur for example at the inner surface of tapered cavity 1c of the catheter body 1 near the distal face of septum 3, which makes it difficult to subsequently flush out any blood, medicament or air bubbles which may flow into this area during use of the catheter. Second, the valve mechanism of FIGS. 1 to 3 has small interstitial spaces/areas within the catheter body 1 into which fluids can flow during use, which give rise to areas of low or no fluid flow. For example, in use fluid can flow between the peripheral surface of the flange 4b and the inner surface 1a of catheter body 1 and into interstitial space 98 between the outer periphery of tubular portion 4a and the inner surface 1a. Third, fluid can flow into interstitial space 99 which is gap 3c between the outer periphery of septum 3 and the inner surface 1a of the catheter body 1. Any fluid present in spaces/areas 98 and 99 is essentially trapped (by septum 3) as there is no easy flow path out of these areas for the fluid to rejoin the main fluid flow. This makes it very difficult to subsequently flush out any blood, medicament or air bubbles which may flow into these areas 98 and 99 during use of the catheter.

A number of valves mechanisms in accordance with various embodiments of the subject invention which improve the flush properties and eliminate or reduce areas of low or no fluid flow occurring within a vascular access device containing a valve mechanism are illustrated in FIGS. 4 to 19.

Figure 4:
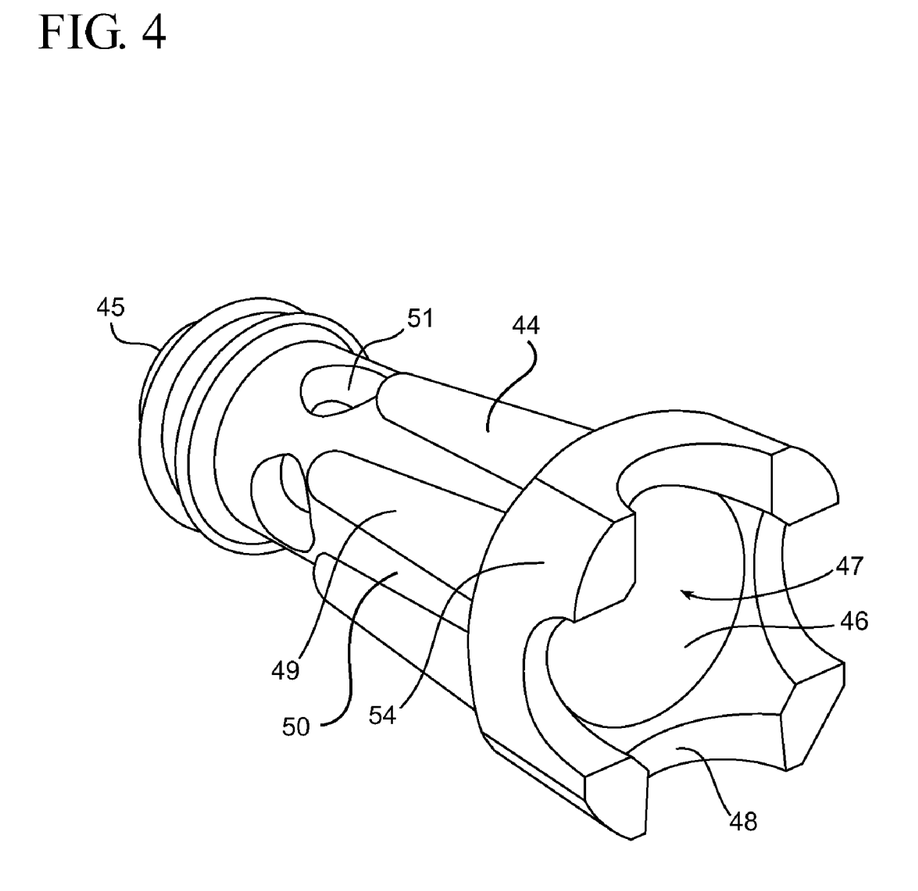
FIG. 4 is a perspective view of a pusher, according to an embodiment of the invention.
Figure 5:
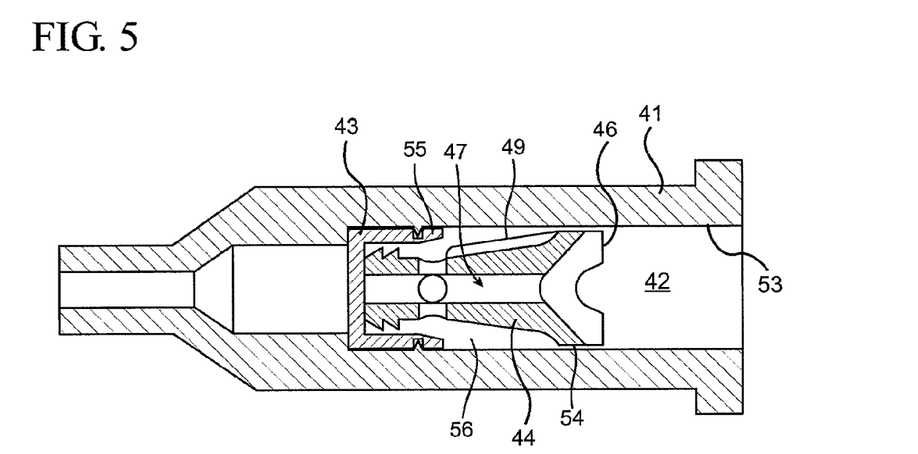
FIG. 5 is a cross section view of a catheter body having the flow control valve mechanism according to the embodiment shown in FIG. 4, with the pusher in the proximal position.
Figure 6:
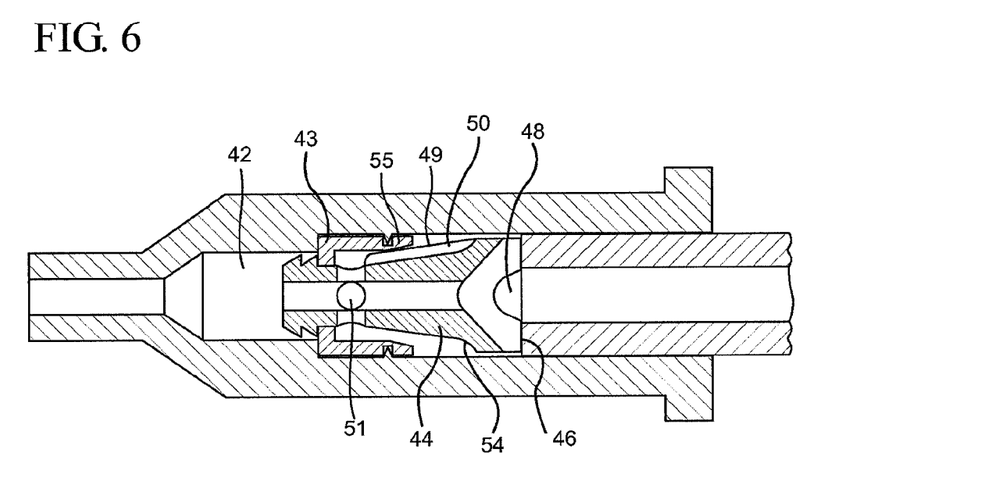
FIG. 6 is a cross section view of a catheter body having a flow control valve mechanism according to the embodiment shown in FIG. 4, with the pusher in the distal position.

FIGS. 4 to 6 show an embodiment of a balanced flow pusher 44 is used to equalize fluid flow evenly both through and around the proximal end of pusher 44. This provides a balanced fluid flow path and better fluid turbulence thus reducing low or no flow fluid areas in order to remove any residual blood from the flashback, aspiration, blood draws.

FIG. 4 shows a pusher 44 having a distal end 45 and a proximal end 46 with a lumen 47 extending therebetween. Flow ports 48 are located at the proximal end 46 of pusher 44, with ribs 49 extending longitudinally along and evenly spaced around the outer surface 54 of pusher 44 to form flow channels 50. Inlet ports 51 are located at the distal end of the flow channels 50 and extend through the side wall of pusher 44. FIG. 5 shows septum 43, which forms a fluid seal in the lumen 42 of catheter body 41 after removal of the needle, with pusher 44 in the proximal position. FIG. 6 shows pusher 44 in the distal position, in which a fluid flowing in distal direction from the proximal end of catheter body 41 can be diverted by four flow ports 48 between the periphery 52 of the proximal end 46 of pusher 44 and the inner surface 53 of lumen 42, along the flow channels 50 and returns to the lumen 47 via four inlet ports 51 equally distributed around the circumference of lumen 47. Septum 43 has a taper 55 on the inner surface to help provide a clear fluid flow path around the outer surface 54 of pusher 44 into the inlet ports 51. Thus, a fluid flow approaching the proximal end 46 of pusher 44 in the distal direction is equally divided, such that a fluid has an equal likelihood of entering the proximal end 46 of lumen 47 of pusher 44 or flowing around the outer surface 54 of pusher 44 before rejoining lumen 47 via inlet ports 51. Thus, the flush properties of this valve mechanism are superior to that of the valve mechanism shown in FIGS. 1 to 3 as there is high fluid flow in the interstitial space 56 between the outer surface 54 of pusher 44 and the inner surface 53 of lumen 42. Additionally, turbulent flow is created within lumen 47 at the confluence of the fluid streams from inlet ports 51.

Figure 7:
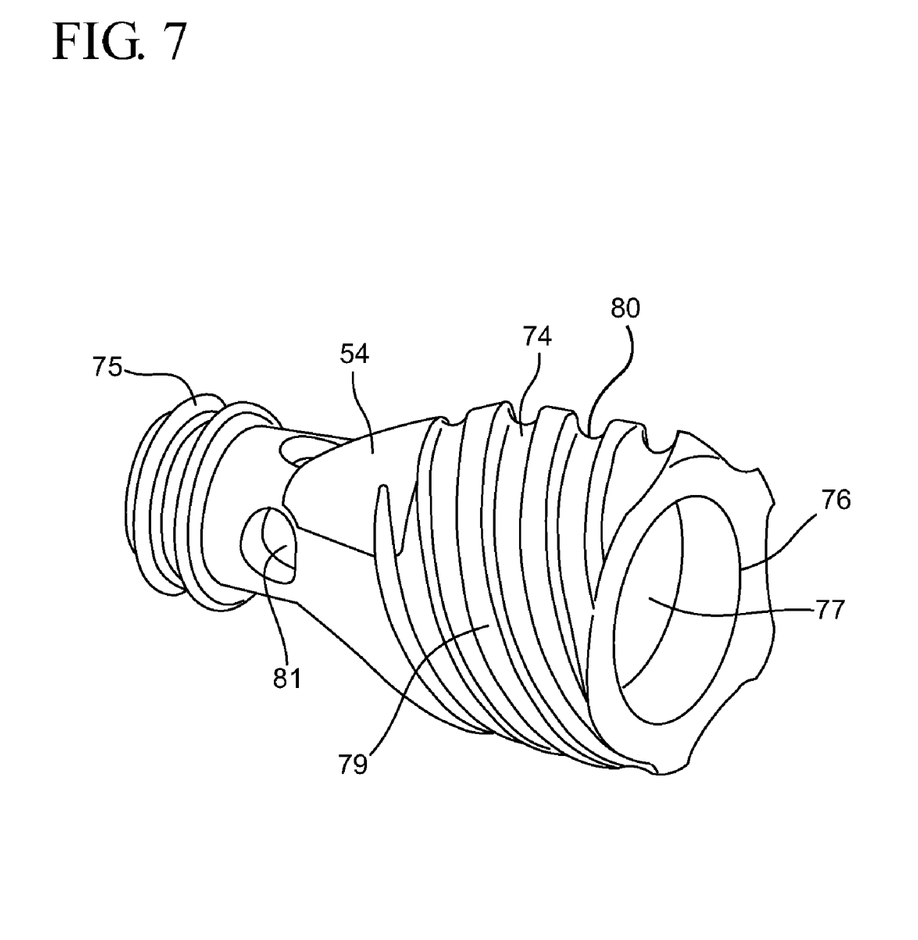
FIG. 7 is a perspective view of a pusher, according to an embodiment of the invention.
Figure 8:
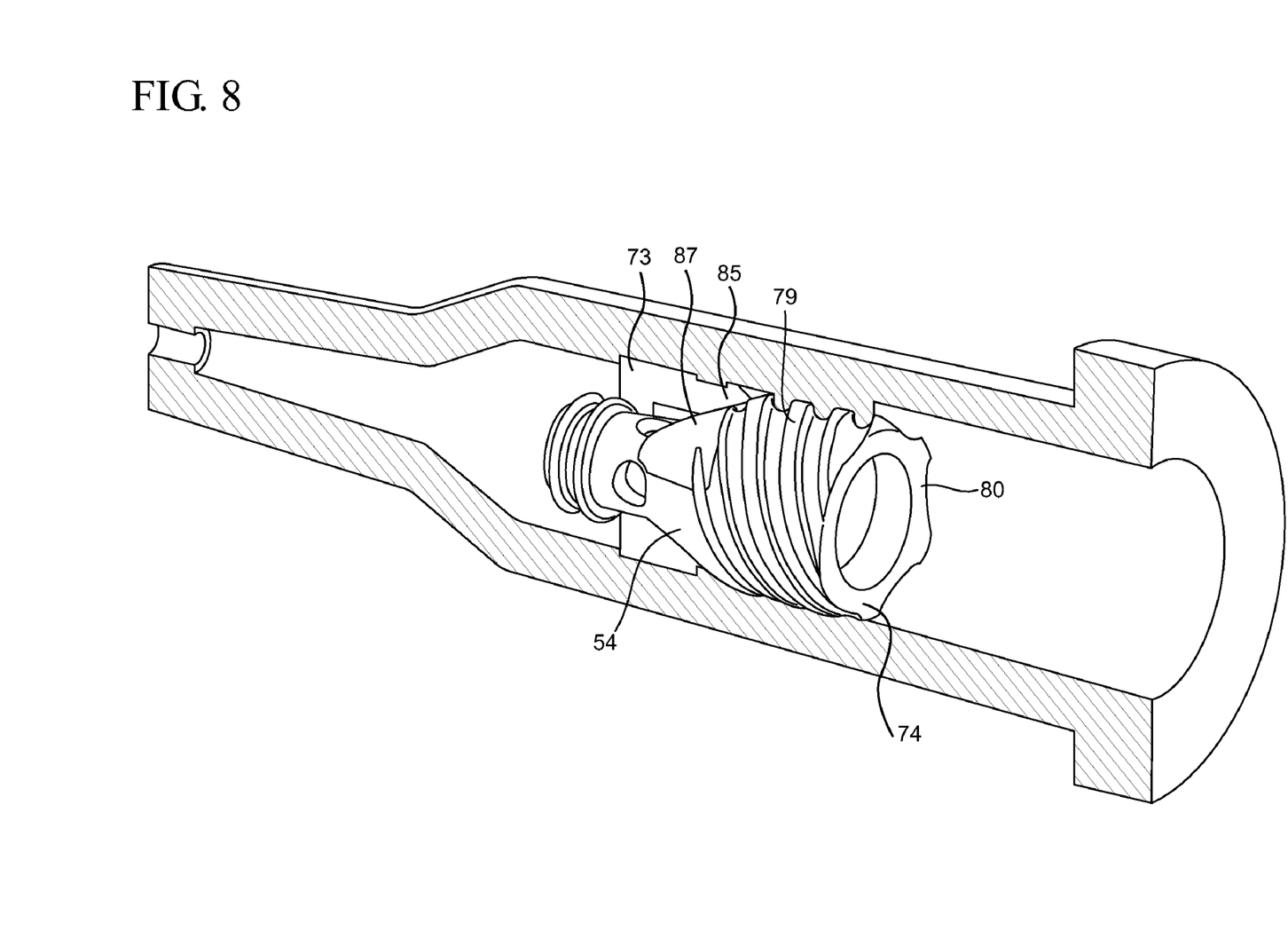
FIG. 8 is a perspective view of a catheter body having a flow control valve mechanism according to the embodiment shown in FIG. 7, with the pusher in the distal position.
Figure 9:
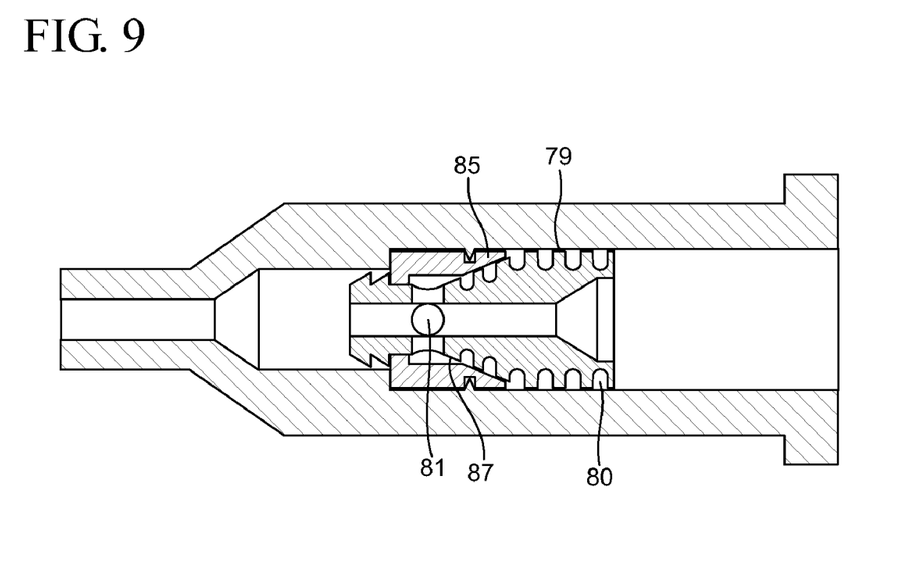
FIG. 9 is a cross section view of a catheter body having a flow control valve mechanism according to the embodiment shown in FIG. 7, with the pusher in the distal position.

FIGS. 7 to 9 show another embodiment of the invention having valve mechanism similar to that shown in FIGS. 4 to 6 which differs by the use of helical flow paths around the outside of the pusher to facilitate a complete flush. FIG. 7 shows a pusher 74 having a distal end 75 and a proximal end 76 with a lumen 77 extending therebetween. Ribs 79 begin at the proximal end 76 of pusher 74, extending helically along and evenly spaced around the outer surface 54 of pusher 74 to form helical flow channels 80. Inlet ports 81 are located at the distal end of the helical flow channels 80 and extend through the side wall of pusher 74. FIGS. 7 to 9 show pusher 74 in the distal position in which fluid can flow either via the lumen 77 of pusher 74 or through the helical channels 80 in the outer surface 54 of pusher 44. Fluid flowing in distal direction from the proximal end of catheter body 41 enters the helical flow channels at the proximal end 76 of pusher 74 and flows along the flow channels 80 and returns to the lumen 77 by four inlet ports 81 equally distributed around the circumference of lumen 77. Septum 73 can also have a taper 85 on the inner surface to mate with a corresponding taper 87 around the outer surface 54 of pusher 74 in order to keep interstitial spaces to a minimum. The use of helical flow channels causes a faster flow rate and a more turbulent flow when compared to a pusher of the same design with straight longitudinal flow channels.

Figure 10:
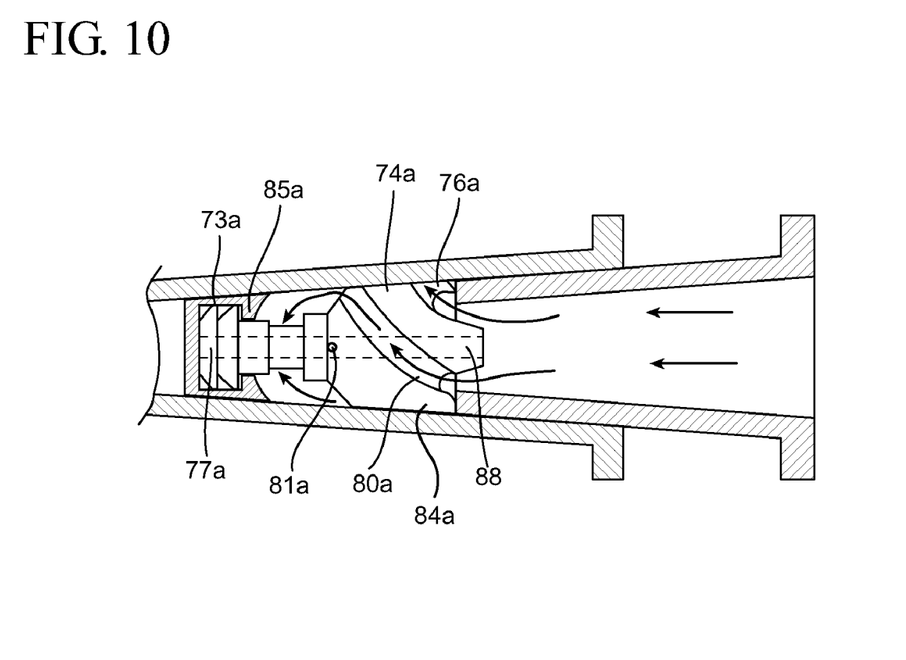
FIG. 10 is a cross section view of a catheter body having a flow control valve mechanism according to an embodiment of the invention, with the pusher in the proximal position.

FIG. 10 shows another embodiment of a valve mechanism with helical flow channels 80a on the outer surface 84a of pusher 74a similar to the embodiment shown in FIGS. 7 to 9. However on removal of the introducer needle a hinged flow deflector 88 is deployed at the proximal end 76a of pusher 74a to restrict or prevent fluid flow through the lumen 77a and divert the majority of fluid flow through the helical flow channels 80a. In addition, there are two inlet ports 81a each of which is approximately quarter of the circumference of the lumen 77a located at the distal end of the helical flow channels 80a. Furthermore septum 73a has a flared face 85a on the inner proximal surface to help direct fluid flow into the inlet ports 81a.

Figure 11:
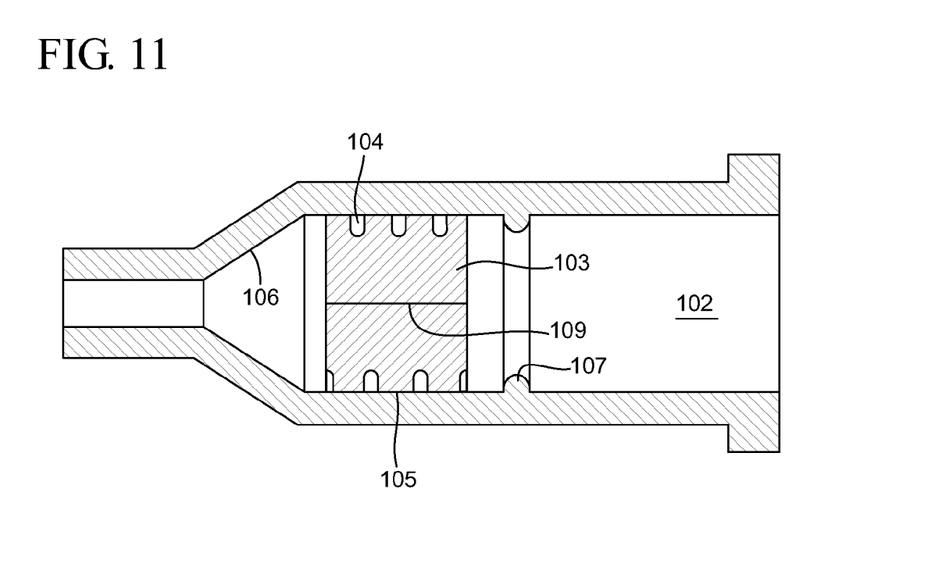
FIG. 11 is a cross section view of a catheter body having a flow control valve mechanism according to an embodiment of the invention.

FIG. 11 shows a further embodiment of a valve mechanism with helical or spiral flow channels. This is a one-piece valve mechanism which only includes a septum and does not use a pusher. The only fluid path in this valve mechanism would be the helical flow channels 104 on the outer surface 105 of the septum 103 which would allow air to escape, minimal blood to escape and then allow for infusion to take place. Slit 109 extends through the septum to facilitate insertion of the introducer needle but forms a fluid seal after the removal of the introducer needle. Septum 103 is retained in position by the combination of taper 106 and annular protrusion 107 of the catheter body lumen 102. It should be noted that the total cross-sectional area of helical flow channels 104 must substantially equal the combined cross-sectional areas of lumen 77 and helical flow channels 80 as shown in the embodiment of FIGS. 7 to 9 as the total fluid flow cross-sectional area must be large enough to prevent a significant flow restriction or pressure build up.

Figure 12:
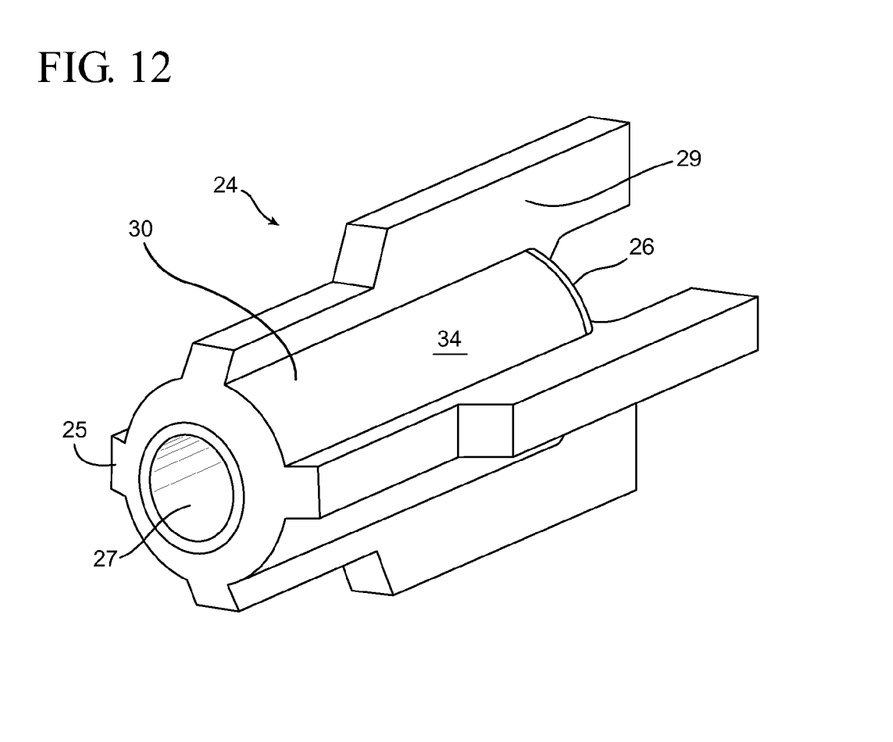
FIG. 12 is a perspective view of a pusher, according to an embodiment of the invention.
Figure 13:
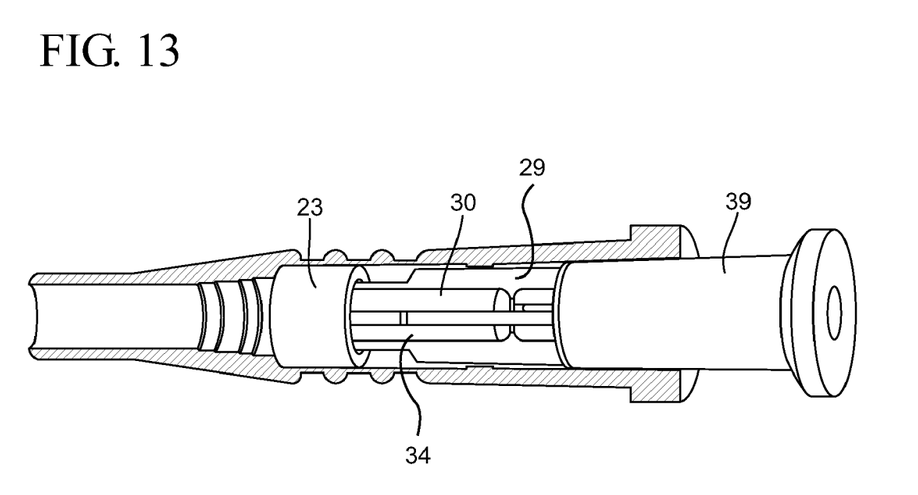
FIG. 13 is a perspective view of a catheter body having a flow control valve mechanism according to the embodiment shown in FIG. 12, with the pusher in the distal position.

FIGS. 12 and 13 show an embodiment of a valve mechanism in which the presence of ribs 29 on the outer surface 34 of pusher 24 allows a parallel coaxial fluid flow to occur both through lumen 27 and between the outer surface 34 of pusher 24 and septum 23. FIG. 13 shows the pusher 24 of FIG. 12 having a distal end 25 and a proximal end 26 with a lumen 27 extending therebetween. Ribs 29 emanate from the distal end 25 of pusher 24, extending along and evenly spaced around the outer surface 34 of pusher 24 to form flow channels 30, and continue past proximal end 26 to provide contact points for a luer connector 39 to act on. Septum 23 is deflected by ribs 29 at the distal end 25 of pusher 24, on reaching distal position. Ribs 29 therefore prevent a radial seal from forming between the outer surface 34 of pusher 24 and septum 23, thus fluid can flow past the septum 23 along flow channels 30 as well as through lumen 27 of pusher 24.

Figure 14:
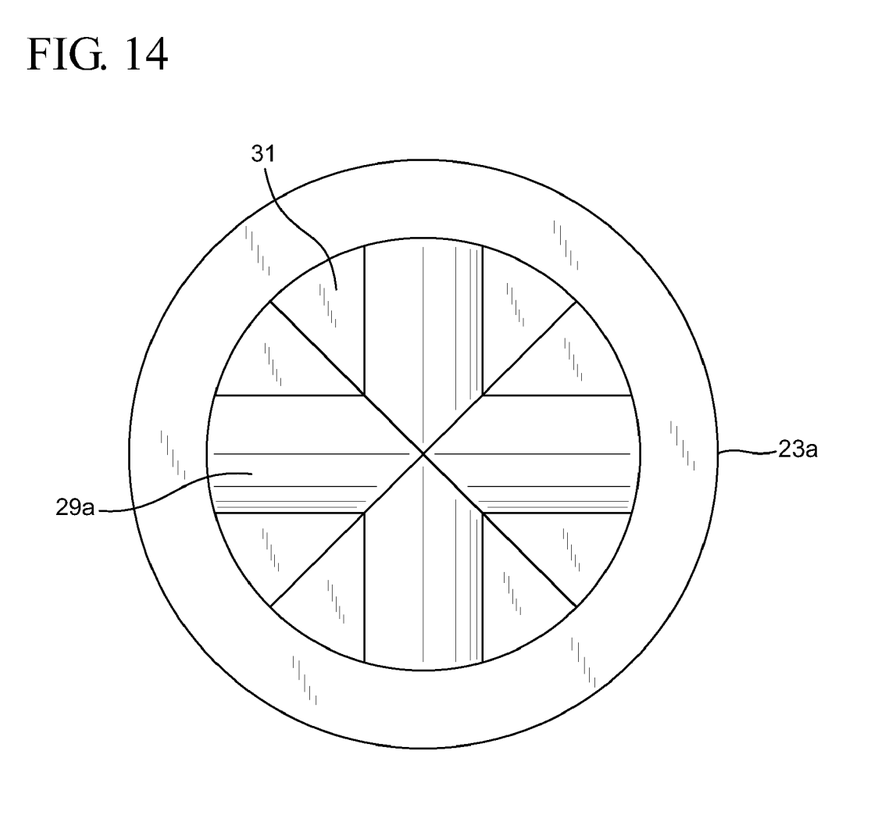
FIG. 14 is a perspective view of a septum, according to an embodiment of the invention.
Figure 15:
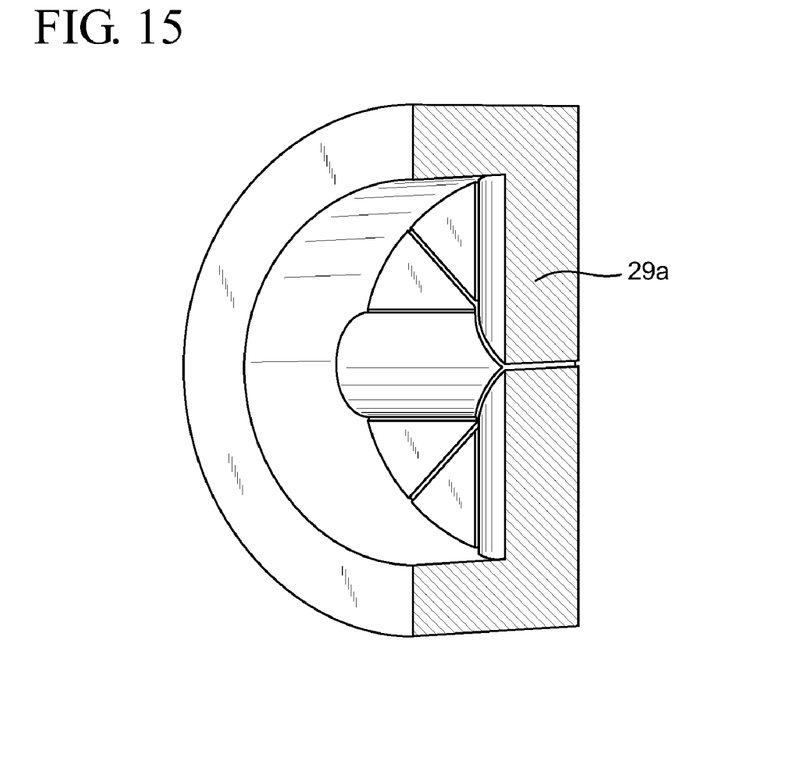
FIG. 15 is a cross section view of a septum, according to the embodiment shown in FIG. 14.

FIGS. 14 and 15 show an alternate embodiment to valve mechanism show in FIGS. 11 to 13 in which ribs 29a are on the proximal face of membrane section 31 of septum 23a instead of the outer surface of pusher.

Figure 16:
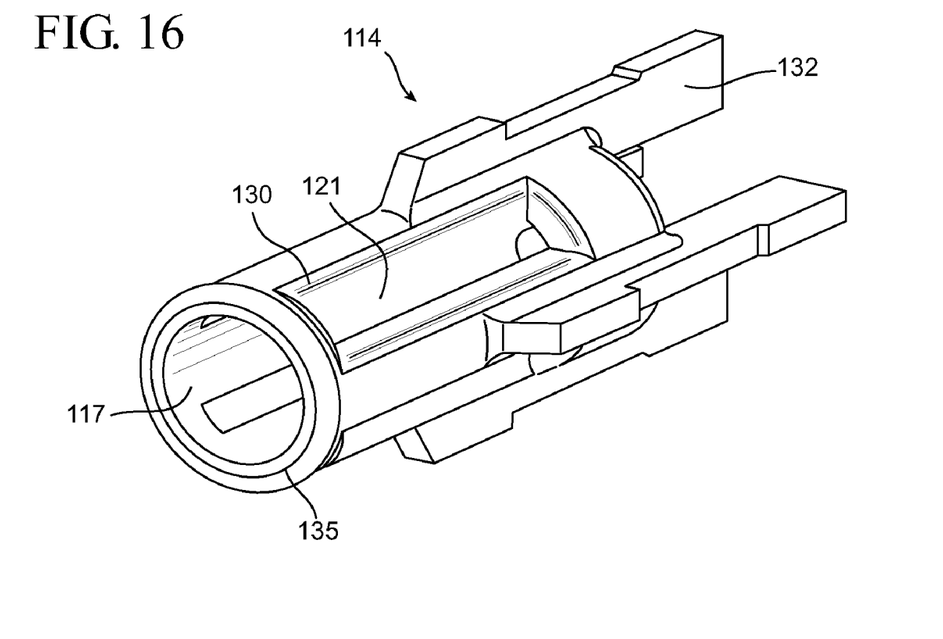
FIG. 16 is a perspective view of a pusher, according to an embodiment of the invention.
Figure 17:
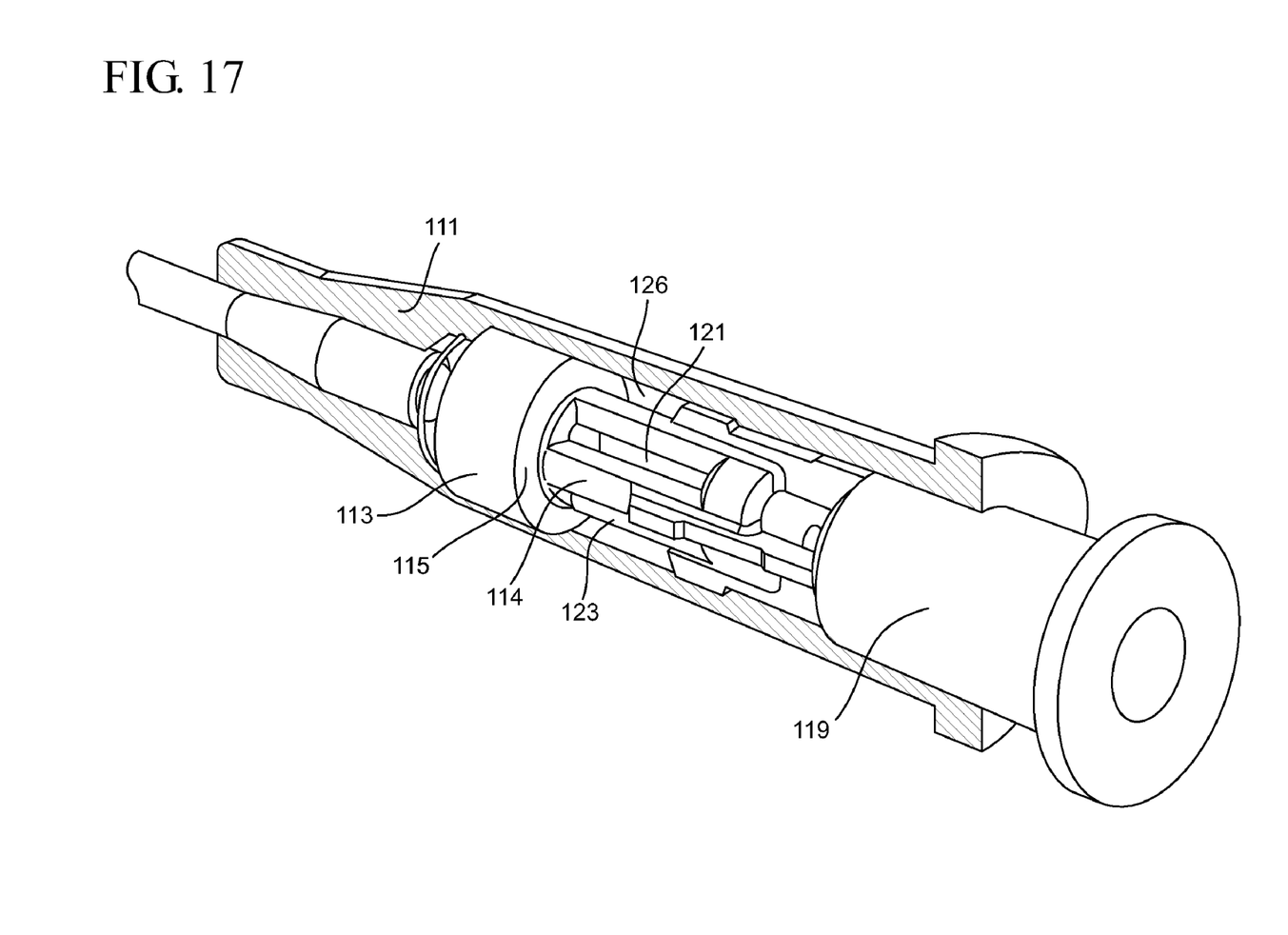
FIG. 17 is a perspective view of a catheter body having a flow control valve mechanism according to the embodiment shown in FIG. 16, with the pusher in the proximal position.
Figure 18:
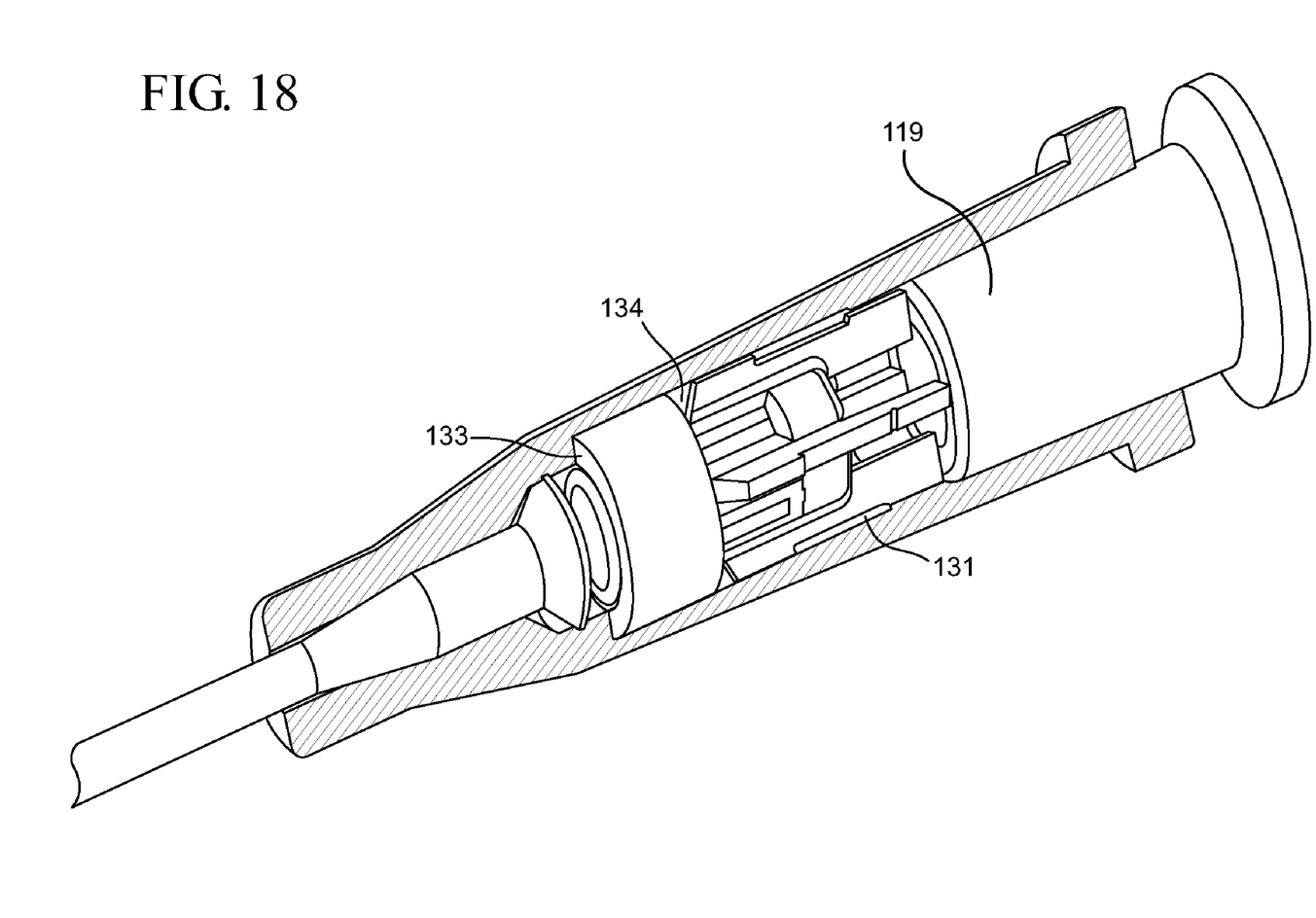
FIG. 18 is a perspective view of a catheter body having a flow control valve mechanism according to the embodiment shown in FIG. 16, with the pusher in the distal position.

FIGS. 16 to 18 show an embodiment of a valve mechanism which gives high flushability due to the openness of the pusher design, and the reversal of the septum orientation. Pusher 114 includes ribs 132 that act as a spacer between a luer connector 119 and lumen 117 to provide sufficient axial length for the fluid flow to spread out from the tip of the luer connector 119 and direct a large portion of the flow through space 126 between pusher 114 and the inner wall 123 of catheter body 111. Fenestrations or longitudinal slots 121 through the sidewall 130 of the pusher 114 allow flushing fluid to reenter the lumen 117 of the pusher 114 while bypassing the septum 113 when pusher 114 is in the distal position (as shown in FIG. 18), then also allow some flow to circulate back out of the pusher 114 to clean the downstream distal side of the septum 113. Ribs 132 interact with undercut 131 in the inner wall 123 of catheter body 111 to retain pusher 114 in the proximal position and with septum 113 to retain pusher 114 in the distal position. The septum 113 is of a generally tubular shape and has the sealing membrane section 115 located at the proximal end 134, instead of the distal end 133 as in a typical septum. This reversed orientation of the membrane section provides a less restrictive flow path as the septum 113 does not enclose the distal end 135 of pusher 114.

Figure 19:
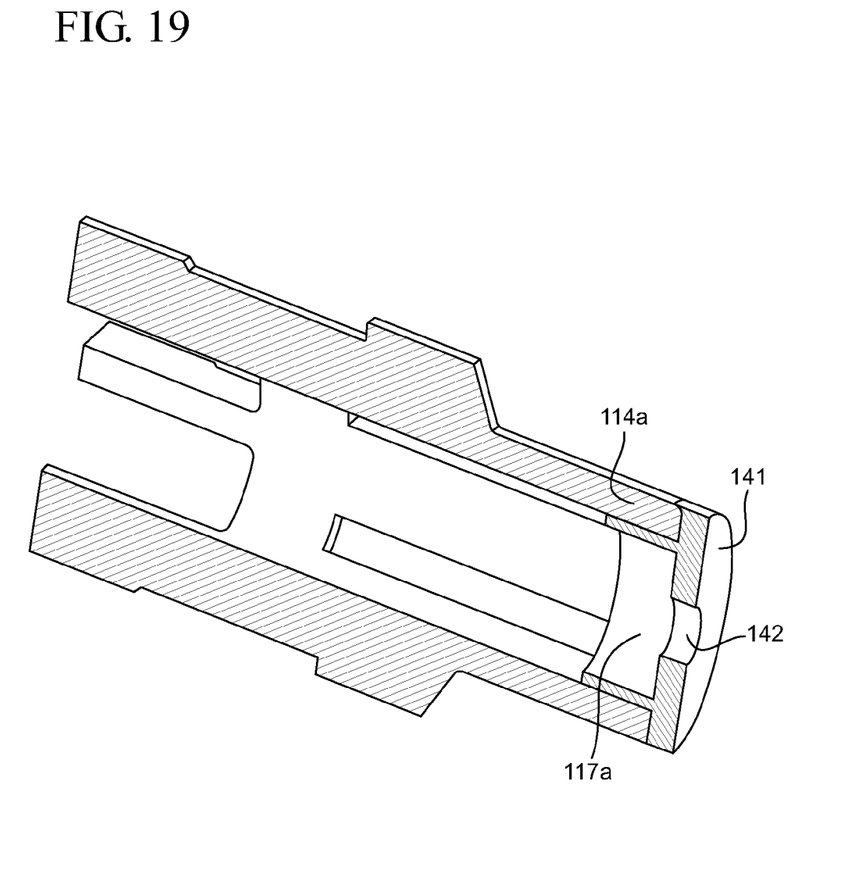
FIG. 19 is a cross section view of a pusher, according to an embodiment of the invention.

FIG. 19 show a further embodiment of a valve mechanism which incorporates an elastomeric stopper 141 to the distal end of pusher 114a to provide a flow restriction to lumen 117a after the needle is removed and force a portion of the flushing fluid to pass along the outside of the pusher 114a, cleaning out any blood or infusant. The balance of the relative flow rate inside lumen 117a and outside of pusher 114a can be controlled by addition and size of a hole 142 in stopper 141 or degree of occlusion of lumen 117a by stopper 141.

Any septum described herein may have a hole present in the center of membrane section sized to produce a specified blood leakage rate if so desired and may be made of a variety of suitable materials and through a variety of suitable manufacturing methods. For example, the septum may be formed from liquid silicone rubber through suitable molding procedures, such as insert molding, injection molding, other molding techniques, or a combination of molding techniques. The septum 103, or any septum described herein, may also include a coating of antimicrobial substance on any of its surfaces, especially those surfaces which have contact with fluid.

Although illustrative embodiments of the present invention have been described herein with reference to the examples, it is to be understood that the invention is not limited to those precise embodiments, and that various other changes and modifications may be effected therein by one skilled in the art without departing from the scope or spirit of the invention.

What is claimed is:

1. A vascular access device, comprising:
    an intravenous catheter adapter having an inner surface, a proximal end, a distal end and a first lumen extending therethrough;
    a septum positioned within the first lumen, the septum dividing the first lumen into a distal portion and a proximal portion;
    a pusher disposed within the proximal portion of the first lumen, the pusher having an outer surface, a distal end, a proximal end, and a second lumen extending therethrough, the outer surface further including a rib that emanates from the distal end of the pusher and extends along the outer surface and past the proximal end of the pusher, a proximal end of the rib comprising a contact point;
    a first flow channel formed between the inner surface of the intravenous catheter adapter and the outer surface of the pusher; and
    a second flow channel comprising the second lumen.

2. The device of claim 1, wherein the rib comprises a plurality of ribs evenly spaced around the outer surface.

3. The device of claim 1, wherein the septum comprises a slit through which the distal end of the pusher is advanced to provide fluid communication between the distal portion of the first lumen and the second lumen.

4. The vascular access device of claim 1, wherein the rib is straight.

5. The vascular access device of claim 1, the pusher further comprising at least one of a fluid diverter, a fenestration, an inlet port and a flow port.

6. The vascular access device of claim 5, wherein the at least one flow port comprises the proximal end of the pusher.

* * * * *